(12) United States Patent
Nakamura et al.

(10) Patent No.: US 8,763,669 B2
(45) Date of Patent: Jul. 1, 2014

(54) APPARATUS FOR MANUFACTURING COMPOSITE SHEET OF ABSORBENT ARTICLE

(71) Applicants: Taishi Nakamura, Kagawa (JP); Shinichi Ishikawa, Kagawa (JP); Jun Okuda, Kagawa (JP)

(72) Inventors: Taishi Nakamura, Kagawa (JP); Shinichi Ishikawa, Kagawa (JP); Jun Okuda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 13/940,832

(22) Filed: Jul. 12, 2013

(65) Prior Publication Data

US 2013/0299096 A1 Nov. 14, 2013

Related U.S. Application Data

(62) Division of application No. 13/262,653, filed as application No. PCT/JP2010/054039 on Mar. 10, 2010.

(30) Foreign Application Priority Data

Apr. 3, 2009 (JP) ................................ 2009-091505

(51) Int. Cl.
*A61F 13/15* (2006.01)
(52) U.S. Cl.
USPC ........... 156/552; 156/324; 156/433; 156/436; 156/439; 156/440; 156/164; 156/229
(58) Field of Classification Search
USPC .......................... 156/324, 436, 439, 440, 433
See application file for complete search history.

(56) References Cited

U.S. PATENT DOCUMENTS

| 5,147,487 A | 9/1992 | Nomura et al. |
| 6,287,409 B1 | 9/2001 | Stephany |
| 6,589,149 B1 | 7/2003 | VanEperen et al. |
| 2002/0023706 A1 | 2/2002 | Vogt et al. |

FOREIGN PATENT DOCUMENTS

| CN | 1345991 A | 4/2002 |
| CN | 1691927 A | 11/2005 |
| JP | 3033201 A | 2/1991 |
| JP | 8280740 A | 10/1996 |

(Continued)

OTHER PUBLICATIONS

International Search Report for PCT/JP2010/054039 dated Jun. 15, 2010.

(Continued)

*Primary Examiner* — Daniel McNally
*Assistant Examiner* — Margaret Squalls
(74) *Attorney, Agent, or Firm* — Lowe Hauptman & Ham LLP

(57) ABSTRACT

A method of manufacturing a composite sheet includes joining a first elastic strip member to a sheet by feeding and surface-contacting the first elastic strip member to a continuous body of the sheet; and joining a second elastic strip member to the sheet by feeding and surface-contacting the second elastic strip member to the continuous body. The first elastic strip member supplied toward a first spindle portion side roller is subsequently put around an outer circumferential face of the first spindle portion side roller and an outer circumferential face of a first oscillating end side roller. The second elastic strip member supplied toward the second spindle portion side roller of a second oscillating arm is subsequently put around an outer circumferential face of a second spindle portion side roller and an outer circumferential face of the second oscillating end side roller of the second oscillating arm.

8 Claims, 9 Drawing Sheets

(56) References Cited

FOREIGN PATENT DOCUMENTS

| | | | |
|---|---|---|---|
| JP | 11322147 A | 11/1999 | |
| JP | 2001178769 A | 7/2001 | |
| JP | 2003517880 A | 6/2003 | |
| JP | 2004505725 A | 2/2004 | |
| JP | 2004159866 A | 6/2004 | |

OTHER PUBLICATIONS

Corresponding EA Application No. 20110144531 Office Action dated Jul. 23, 2013.

B-B ARROW VIEW

APPARATUS FOR MANUFACTURING COMPOSITE SHEET OF ABSORBENT ARTICLE

RELATED APPLICATION

The present application is a Divisional of U.S. patent application Ser. No. 13/262,653, filed Dec. 9, 2011, and is based on International Application Number PCT/JP2010/054039 filed Mar. 10, 2010, and claims priority from, Japanese Application Number 2009-91505, filed Apr. 3, 2009, the disclosures of which is hereby incorporated by reference herein in its entirety.

TECHNICAL FIELD

The present invention relates to manufacturing methods and manufacturing apparatuses of composite sheets of absorbent articles.

BACKGROUND ART

A disposable diaper and the like have conventionally been known as an example of an absorbent article that absorbs body waste fluid. In its manufacturing line, a continuous body of a sheet that is transported continuously in a transporting direction is attached continuously with a continuous body of an elastic member in a meander pattern such as a sine curve.

As an example of such an attaching method, PTL 1 discloses attaching an elastic member to the sheet while oscillating it, by arranging an oscillating arm that oscillates in a direction intersecting a transporting direction of a sheet in the vicinity of a transporting path of a sheet, and passing a thread-like elastic member through a through hole in an oscillating end of the oscillating arm.

Further, PTL 2 discloses, as shown in a perspective view of FIG. 1A, putting an elastic member 221 around a rolling roller 203 that rolls around an outer circumferential face of a transfer roll 201, by reciprocating the rolling roller 203 in a rotational axis C201 direction of the transfer roll 201, the elastic member 221 is sucked and held in a meander pattern such as a sine curve on an outer circumferential face of the transfer roll 201, and then a sheet 231 is made to contact the outer circumferential face of the transfer roll 201 to handover the elastic member 221 to the sheet 231 and to attach it thereon.

CITATION LIST

Patent Literature

PTL1: JP-A2004-159866
PTL2: JP-T-2003-517880

SUMMARY OF INVENTION

Technical Problem

In the case of using a strip member with a certain width (hereafter, also referred to as an elastic strip member) as the above described elastic member, however, with the above method in PTL1, the elastic strip member is folded when passing the through hole in the oscillating end and the like, and as a result, it is difficult to make the elastic strip member surface-contact the sheet and attach it thereon.

On the other hand, with the method in PTL2, the elastic member 221 is put around the outer circumferential face of the rolling roller 203, therefore even in the case where the elastic member 221 is the elastic strip member, the elastic strip member 221 can be maintained in a flat state and transferred to the transfer roll 201, and as a result, the elastic strip member 221 can be made to surface-contact the sheet 231 and be attached thereon.

As shown in for example FIG. 1B, however, when arranging a pair of the elastic strip members 221, 221 in a CD direction that is orthogonal to the transporting direction, and attaching them to sheet 231 in an arrangement pattern in which these elastic strip members 221, 221 intersect each other partially, as shown in FIG. 1A, these rolling rollers 203, 203 are aligned in the same positions in a circumferential direction of the transfer roll 201, so that they will collide against each other when reciprocating in the CD direction. As a result, the elastic strip member 221 cannot be attached in such an arrangement pattern.

The present invention has been made in view of the above conventional problems, and an object is to provide a manufacturing method and a manufacturing apparatus of a composite sheet of an absorbent article in which surface-contact of at least a continuous body of a pair of elastic strip members to a continuous body of the sheet can be certainly achieved, when surface-contacting and attaching each of at least the continuous body of the pair of elastic strip members to the continuous body of the sheet in a predetermined meander pattern, and in which these elastic strip members can be attached to the sheet without any problem in an arrangement pattern in which the elastic strip members partially intersect or are close to each other.

Solution to Problem

An aspect of the invention to achieve the above advantages is a manufacturing method of a composite sheet of an absorbent article in which a continuous body of an elastic strip member is joined in a predetermined meander pattern in respect to a continuous body of a sheet that is continuously transported in a transporting direction, the method comprising:

a first joining of joining a continuous body of a first elastic strip member to a continuous body of a sheet by feeding and surface-contacting the continuous body of the first elastic strip member to the continuous body of the sheet, via a first oscillating arm that oscillates in a direction intersecting the transporting direction with a first spindle portion as a swivel center; and a second joining of joining a continuous body of a second elastic strip member to the continuous body of the sheet by feeding and surface-contacting the continuous body of the second elastic strip member to the continuous body of the sheet, via a second oscillating arm that oscillates in a direction intersecting the transporting direction with a second spindle portion as a swivel center, wherein the first oscillating arm includes a first oscillating end side roller provided to an oscillating end side of the first oscillating arm and a first spindle portion side roller provided to the first spindle portion side, wherein the second oscillating arm includes a second oscillating end side roller provided to an oscillating end side of the second oscillating arm and a second spindle portion side roller provided to the second spindle portion side, wherein in the first joining, the continuous body of the first elastic strip member supplied toward the first spindle portion side roller through a first supply route is subsequently put around an outer circumferential face of the first spindle portion side roller and an outer circumferential face of the first oscillating end side roller, and, after being reversed in a travel direction with the first oscillating end side roller, is placed on the continuous body of the sheet and joined thereon, wherein in the second joining, the continuous body of the second elastic strip member supplied toward the second spindle portion side roller through a second supply route is subsequently put around an outer circumferential face of the second spindle portion side roller and an outer circumferential face of the second oscillating end side roller, and, after being reversed in the travel direction with the second oscillating end side roller, is placed on the continuous body of the sheet and joined thereon, wherein a first placing position where the continuous body of the first elastic strip member is to be placed on the continuous body of the sheet with the first oscillating arm and a second placing position where the continuous body of the second elastic strip member is to be placed on the continuous body of the sheet with the second oscillating arm are different from each other in the transporting direction.

Further, a manufacturing apparatus of a composite sheet of an absorbent article that joins a continuous body of an elastic strip member in a predetermined meander pattern to a continuous body of a sheet continuously transported in a transporting direction, the apparatus comprising:

a first guide member that joins a continuous body of a first elastic strip member to a continuous body of a sheet by feeding and surface-contacting the continuous body of the first elastic strip member to the continuous body of the sheet, via a first oscillating arm that oscillates in a direction intersecting the transporting direction with a first spindle portion as a swivel center; and a second guide member that joins a continuous body of a second elastic strip member to the continuous body of the sheet by feeding and surface-contacting the continuous body of the second elastic strip member to the continuous body of the sheet, via a second oscillating arm that oscillates in a direction intersecting the transporting direction with a second spindle portion as a swivel center, wherein the first oscillating arm includes a first oscillating end side roller provided to an oscillating end side of the first oscillating arm and a first spindle portion side roller provided to the first spindle portion side, wherein the second oscillating arm includes a second oscillating end side roller provided to an oscillating end side of the second oscillating arm and a second spindle portion side roller provided to the second spindle portion side, wherein the continuous body of the first elastic strip member supplied toward the first spindle portion side roller through a first supply route is subsequently put around an outer circumferential face of the first spindle portion side roller and an outer circumferential face of the first oscillating end side roller, and, after being reversed in a travel direction with the first oscillating end side roller, is placed on the continuous body of the sheet and joined thereon, wherein the continuous body of the second elastic strip member supplied toward the second spindle portion side roller through a second supply route is subsequently put around an outer circumferential face of the second spindle portion side roller and an outer circumferential face of the second oscillating end side roller, and, after being reversed in the travel direction with the second oscillating end side roller, is placed on the continuous body of the sheet and joined thereon, wherein a first placing position where the continuous body of the first elastic strip member is to be placed on the continuous body of the sheet with the first oscillating arm and a second placing position where the continuous body of the second elastic strip member is to be placed on the continuous body of the sheet with the second oscillating arm are different from each other in the transporting direction.

Advantageous Effects of Invention

According to this invention, surface-contact of at least a continuous body of a pair of the elastic strip members to a continuous body of the sheet can be certainly achieved, when surface-contacting and attaching each of at least the continuous body of the pair of the elastic strip members to the continuous body of the sheet in a predetermined meander pattern, and these elastic strip members can be attached to the sheet without any problem in an arrangement pattern in which the elastic strip members partially intersect or are close to each other.

DESCRIPTION OF EMBODIMENTS

Figure 1A:
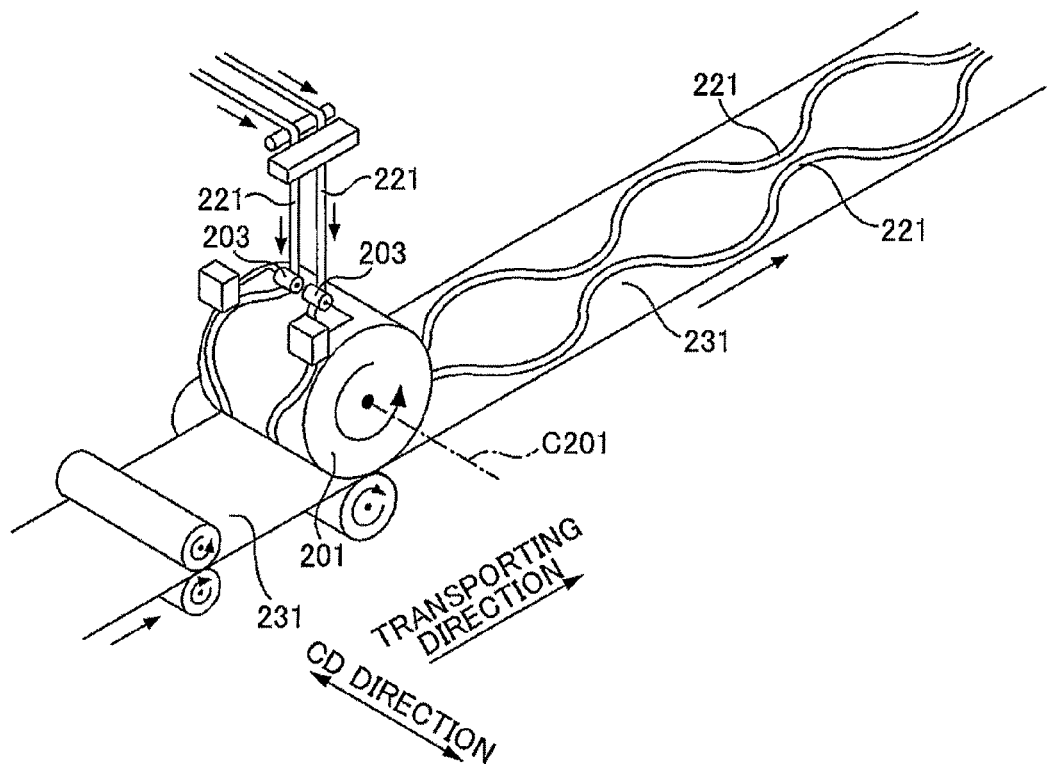
FIG. 1A is a perspective view of a known method of attaching a continuous body of an elastic strip member 221 in a predetermined meander pattern in respect to a continuous body of a sheet 231.

With the description in this specification and the attached drawings, at least the matters below will become clear.

A manufacturing method of a composite sheet of an absorbent article in which a continuous body of an elastic strip member is joined in a predetermined meander pattern in respect to a continuous body of a sheet that is continuously transported in a transporting direction, the method including:

a first joining of joining a continuous body of a first elastic strip member to a continuous body of a sheet by feeding and surface-contacting the continuous body of the first elastic strip member to the continuous body of the sheet, via a first oscillating arm that oscillates in a direction intersecting the transporting direction with a first spindle portion as a swivel center; and a second joining of joining a continuous body of a second elastic strip member to the continuous body of the sheet by feeding and surface-contacting the continuous body of the second elastic strip member to the continuous body of the sheet, via a second oscillating arm that oscillates in a direction intersecting the transporting direction with a second spindle portion as a swivel center, wherein the first oscillating arm includes a first oscillating end side roller provided to an oscillating end side of the first oscillating arm and a first spindle portion side roller provided to the first spindle portion side, wherein the second oscillating arm includes a second oscillating end side roller provided to an oscillating end side of the second oscillating arm and a second spindle portion side roller provided to the second spindle portion side, wherein in the first joining, the continuous body of the first elastic strip member supplied toward the first spindle portion side roller through a first supply route is subsequently put around an outer circumferential face of the first spindle portion side roller and an outer circumferential face of the first oscillating end side roller, and, after being reversed in a travel direction with the first oscillating end side roller, is placed on the continuous body of the sheet and joined thereon, wherein in the second joining, the continuous body of the second elastic strip member supplied toward the second spindle portion side roller through a second supply route is subsequently put around an outer circumferential face of the second spindle portion side roller and an outer circumferential face of the second oscillating end side roller, and, after being reversed in the travel direction with the second oscillating end side roller, is placed on the continuous body of the sheet and joined thereon, wherein a first placing position where the continuous body of the first elastic strip member is to be placed on the continuous body of the sheet with the first oscillating arm and a second placing position where the continuous body of the second elastic strip member is to be placed on the continuous body of the sheet with the second oscillating arm are different from each other in the transporting direction.

With the manufacturing method of the composite sheet of the absorbent article, the first placing position of the first oscillating arm and the second placing position of the second oscillating arm are different from each other in the transporting direction of the sheet, so that interference between the first elastic strip member and the second elastic strip member when oscillating can be avoided. As a result, even with an arrangement pattern in which the meander pattern of the first elastic strip member to be attached to the sheet with the first oscillating arm and the meander pattern of the second elastic strip member to be attached to the sheet with the second oscillating arm partially intersect each other or come close to each other, these first and second elastic strip members can be attached without any problem.

Further, the first elastic strip member and the second elastic strip member are each placed on the sheet, after being reversed in the travel direction with the first oscillating end side roller and the second oscillating end side roller. Then, when reversing, each of these first and second elastic strip members are wrapped around the outer circumferential face of the first and the second oscillating end side roller with a predetermined wraparound angle, and with the outer circumferential face, each of these elastic strip members are restrained in a flat shape, and as a result are maintained in a flat shape in the first and the second placing positions. Thus, the first and the second elastic strip members can be certainly surface-contacted and joined to the sheet.

A manufacturing method of a composite sheet of an absorbent article, preferably wherein the continuous body of the sheet is wrapped in a predetermined wraparound angle around an outer circumferential face of a transporting roll that rotates around a predetermined rotational axis with a direction along the transporting direction as a circumferential direction and transported, wherein both the first placing position of the first oscillating arm and the second placing position of the second oscillating arm are set within a range of the wraparound angle, wherein the second placing position is set to a downstream side than the first placing position in the circumferential direction, wherein the second oscillating arm is arranged in a position where the first oscillating arm has rotationally moved to a downstream side in the circumferential direction by only a predetermined rotating angle (excluding 0° and 360°) around an imaginary axis parallel to the rotational axis of the transporting roll.

With the manufacturing method of the composite sheet of the absorbent article, making the manufacturing apparatus of the manufacturing method compact, and improving a joining position precision of the first elastic strip member and the second elastic strip member on the sheet can be both successfully achieved. The details are as below.

The second oscillating arm is arranged in a position where the first oscillating arm has been rotatingly moved by just the rotating angle around an imaginary axis. Thus, while certainly avoiding interference between the first oscillating arm and the second oscillating arm, the size of a space needed to avoid the interference can be made small. As a result, the manufacturing apparatus of the manufacturing method can be made compact.

Further, with the rotational movement, a relative positional relationship between the first oscillating end side roller and the transporting roll, and between the second oscillating end side roller and the transporting roll are substantially maintained. Thus, both the first oscillating end side roller and the second oscillating end side roller can each be closely arranged to the transporting roll, and therefore both the first elastic strip member and the second elastic strip member can be attached at a high precision to the target joining position on the sheet.

A manufacturing method of a composite sheet of an absorbent article, wherein preferably the rotating angle is an arbitrary value in a range of 30° to 150°.

With the manufacturing method of the composite sheet of the absorbent article, making the manufacturing apparatus of the manufacturing method compact and improving the joining position precision of the first elastic strip member and the second elastic strip member on the sheet can be both successfully certainly achieved.

A manufacturing method of a composite sheet of an absorbent article, preferably wherein the continuous body of the sheet is wrapped in a predetermined wraparound angle around an outer circumferential face of a transporting roll that rotates around a predetermined rotational axis, with a direction along the transporting direction as a circumferential direction, and transported, wherein both the first placing position of the first oscillating arm and the second placing position of the second oscillating arm are set within the wraparound angle range, wherein a rotational central axis of the first spindle portion of the first oscillating arm and a rotational central axis of the second spindle portion of the second oscillating arm are facing directions intersecting each other in an imaginary plane with the rotational axis direction of the transporting roll as a direction of the normal.

With the manufacturing method of the composite sheet of the absorbent article, the first oscillating arm and the second oscillating arm are arranged so as to intersect with each other in the imaginary plane. Thus, while certainly avoiding interference between the first oscillating arm and the second oscillating arm, the size of a space needed to avoid the interference can be made smaller. As a result, the manufacturing apparatus of the manufacturing method can be made compact.

A manufacturing method of a composite sheet of an absorbent article, preferably wherein the continuous body of the sheet is wrapped in a predetermined wraparound angle around an outer circumferential face of a transporting roll that rotates around a predetermined rotational axis, with a direction along the transporting direction as a circumferential direction, and transported, wherein both the first placing position of the first oscillating arm and the second placing position of the second oscillating arm are set in a region to an upstream side than a middle position in the circumferential direction within the wraparound angle.

With the manufacturing method of the composite sheet of the absorbent article, a region in which the first elastic strip member and the second elastic strip member are overlapped and pressed on the sheet on the transporting roll can be widely obtained along the circumferential direction of the transporting roll, and as a result, the first elastic strip member and the second elastic strip member can be strongly joined on the sheet.

A manufacturing method of a composite sheet of an absorbent article, preferably wherein the first supply route is along a rotational central axis direction of the first spindle portion of the first oscillating arm, wherein the second supply route is along a rotational central axis direction of the second spindle portion of the second oscillating arm.

With the manufacturing method of the composite sheet of the absorbent article, the first elastic strip member is fed to the first spindle portion side roller along the rotational central axis direction of the first spindle portion. Thus, movement in an intersecting direction of the first elastic strip member that may occur due to the oscillating movement of the first oscillating arm mainly appears as a twist of a portion of the first elastic strip member positioned to the upstream side than the first spindle portion side roller and is absorbed therein, and thus the falling off of the first elastic strip member from the first spindle portion side roller can be effectively prevented.

Similarly, the second elastic strip member is fed to the second spindle portion side roller along the rotational central axis direction of the second spindle portion. Thus, movement of the second elastic strip member in the intersecting direction that may occur due to the oscillation movement of the second oscillating arm mainly appears as a twist of a portion of the second elastic strip member positioned in the upstream side than the second spindle portion side roller and is absorbed therein, and thus the falling off of the second elastic strip member from the second spindle portion side roller can be effectively prevented.

A manufacturing method of a composite sheet of an absorbent article, preferably wherein the rotational central axis of the first spindle portion of the first oscillating arm is in contact with the outer circumferential face of the first spindle portion side roller of the first oscillating arm, wherein the rotational central axis of the second spindle portion of the second oscillating arm is in contact with the outer circumferential face of the second spindle portion side roller of the second oscillating arm.

With the manufacturing method of the composite sheet of the absorbent article, the rotational central axis of the first spindle portion is in contact with the outer circumferential face of the first spindle portion side roller. Thus, the first elastic strip member is certainly fed to the first spindle portion side roller along the rotational central axis direction of the first spindle portion. As a result, the movement of the first elastic strip member in the intersecting direction that may occur due to the oscillating movement of the first oscillating arm certainly appears as a twist in a portion of the first elastic strip member to the upstream side than the first spindle portion side roller and is absorbed therein, and as a result the falling off of the first elastic strip member from the first spindle portion side roller is effectively prevented.

Similarly, the rotational central axis of the second spindle portion is in contact with the outer circumferential face of the second spindle portion side roller. Thus, the second elastic strip member is certainly fed to the second spindle portion side roller along the rotational central axis direction of the second spindle portion. As a result, the movement of the second elastic strip member in the intersecting direction that may occur due to the oscillation movement of the second oscillating arm, certainly appears as a twist in a portion of the second elastic strip member to the upstream side than the second spindle portion side roller and is absorbed therein, and as a result the falling off of the second elastic strip member from the second spindle portion side roller is effectively prevented.

A manufacturing method of a composite sheet of an absorbent article, preferably wherein the continuous body of the sheet is wrapped in a predetermined wraparound angle around an outer circumferential face of a transporting roll that rotates around a predetermined rotational axis, with a direction along the transporting direction as a circumferential direction, and transported, wherein both the first placing position of the first oscillating arm and the second placing position of the second oscillating arm are set within the wraparound angle range, wherein a first oscillating end side roller and the first spindle portion of the first oscillating arm are arranged to sandwich the rotational axis of the transporting roll together, wherein a second oscillating end side roller and the second spindle portion of the second oscillating arm are arranged to sandwich the rotational axis of the transporting roll together.

With the manufacturing method of the composite sheet of the absorbent article, the travel direction of each of the first elastic strip member and the second elastic strip member are reversed with the first oscillating roller and the second oscillating roller, and subsequently each elastic strip member can be wrapped around the outer circumferential face of the transporting roll. Thus, both the first elastic strip member and the second elastic strip member can be maintained in a flat state, and placed to the sheet, and as a result each elastic strip member can be certainly surface-contacted and attached to the sheet.

A manufacturing apparatus of a composite sheet of an absorbent article that joins a continuous body of an elastic strip member in a predetermined meander pattern to a continuous body of a sheet continuously transported in a transporting direction, the apparatus including:

a first guide member that joins a continuous body of a first elastic strip member to a continuous body of a sheet by feeding and surface-contacting the continuous body of the first elastic strip member to the continuous body of the sheet, via a first oscillating arm that oscillates in a direction intersecting the transporting direction with a first spindle portion as a swivel center; and a second guide member that joins a continuous body of a second elastic strip member to the continuous body of the sheet by feeding and surface-contacting the continuous body of the second elastic strip member to the continuous body of the sheet, via a second oscillating arm that oscillates in a direction intersecting the transporting direction with a second spindle portion as a swivel center, wherein the first oscillating arm includes a first oscillating end side roller provided to an oscillating end side of the first oscillating arm and a first spindle portion side roller provided to the first spindle portion side, wherein the second oscillating arm includes a second oscillating end side roller provided to an oscillating end side of the second oscillating arm and a second spindle portion side roller provided to the second spindle portion side, wherein the continuous body of the first elastic strip member supplied toward the first spindle portion side roller through a first supply route is subsequently put around an outer circumferential face of the first spindle portion side roller and an outer circumferential face of the first oscillating end side roller, and, after being reversed in a travel direction with the first oscillating end side roller, is placed on the continuous body of the sheet and joined thereon, wherein the continuous body of the second elastic strip member supplied toward the second spindle portion side roller through a second supply route is subsequently put around an outer circumferential face of the second spindle portion side roller and an outer circumferential face of the second oscillating end side roller, and, after being reversed in the travel direction with the second oscillating end side roller, is placed on the continuous body of the sheet and joined thereon, wherein a first placing position where the continuous body of the first elastic strip member is to be placed on the continuous body of the sheet with the first oscillating arm and a second placing position where the continuous body of the second elastic strip member is to be placed on the continuous body of the sheet with the second oscillating arm are different from each other in the transporting direction.

With the manufacturing apparatus of the composite sheet of the absorbent article, the first placing position of the first oscillating arm and the second placing position of the second oscillating arm are different from each other in the transporting direction of the sheet, so that interference between the first elastic strip member and the second elastic strip member when oscillating can be avoided. As a result, even in an arrangement pattern in which the meander pattern of the first elastic strip member to be attached to the sheet with the first oscillating arm and the meander pattern of the second elastic strip member to be attached to the sheet with the second oscillating arm partially intersect or come close to each other, these first and second elastic strip members can be attached without any problem.

Further, each of the first elastic strip member and the second elastic strip member is placed on the sheet, after being reversed in the travel direction by each of the first oscillating end side roller and the second oscillating end side roller. When reversing, each of the first and the second elastic strip members is wrapped at a predetermined wraparound angle around the outer circumferential face of the first and the second oscillating end side roller, so that each of the elastic strip members is restrained in a flat shape with the outer circumferential face, and as a result are maintained in a flat shape in the first and the second placing positions. Thus, the first and the second elastic strip members can be certainly surface-contacted and joined to the sheet.

The Present Embodiment

A manufacturing method and a manufacturing apparatus of a sheet of the present embodiment is applied to, for example, a manufacturing line of a disposable diaper 1 (corresponds to an absorbent article).

Diaper 1

Figure 2A:
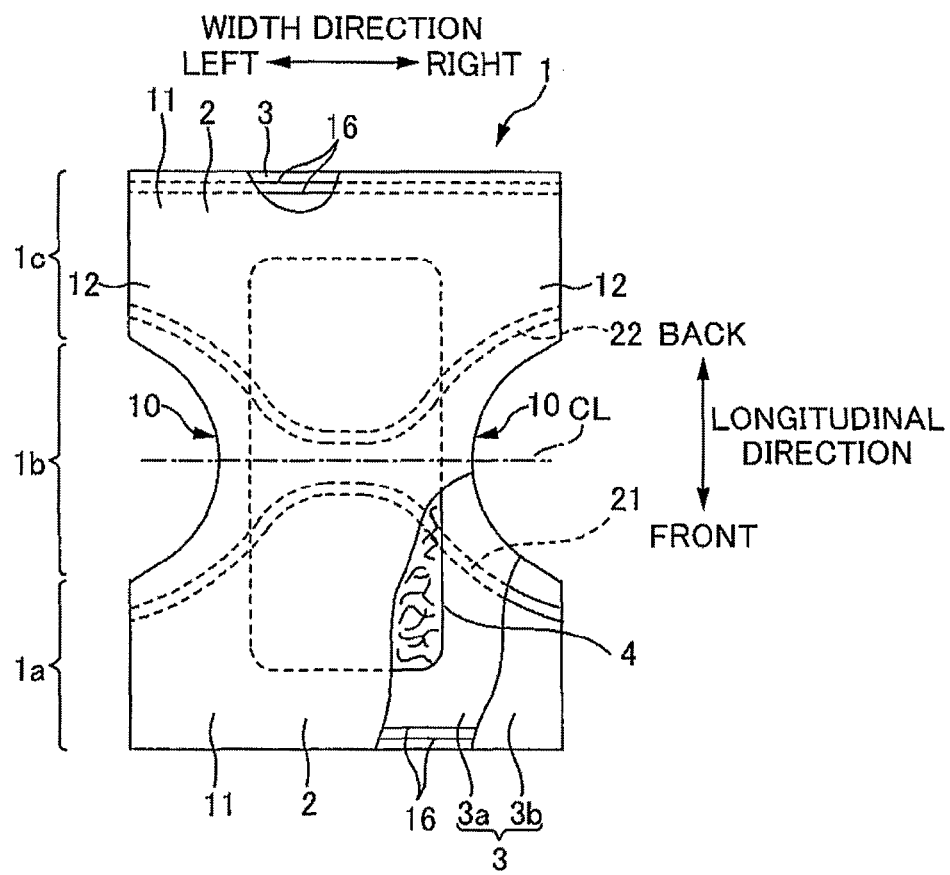
FIG. 2A is a partially cutaway plan view of a diaper 1.
Figure 2B:
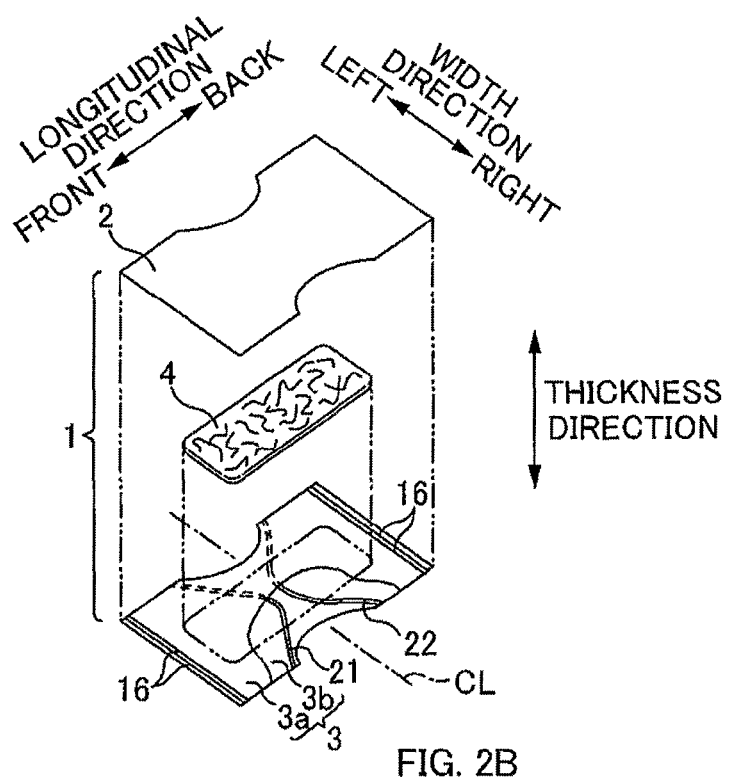
FIG. 2B is an exploded perspective view of the diaper.

FIG. 2A is a partially cutaway plan view of a diaper 1, and FIG. 2B is an exploded perspective view of the diaper. Both diagrams show an expanded state in which a front torso area 1a and a back torso area 1c in a flank portion of a pants-type diaper 1 are separated.

This diaper 1 has a longitudinal direction and a width direction and a thickness direction, that are perpendicular to each other, and along the longitudinal direction of the diaper 1 are defined the front torso area 1a, a crotch area 1b, and the back torso area 1c. Further, the diaper 1 has in the thickness direction, a fluid permeable surface sheet 2, a fluid impermeable back face sheet 3, and a fluid-absorbent absorbent body 4 arranged in between the sheets 2, 3. The surface sheet 2 and the back face sheet 3 are overlapped in a portion extending outward from a peripheral edge of the absorbent body 4, and joined to each other by such as a hot-melt adhesive. Thereby, end edge portion flaps 11 are formed to the front and back in the longitudinal direction and side edge portion flaps 12 are formed to the left and right in the width direction. Note that, in the crotch area 1b of the side edge portion flaps 12, are formed around-leg concave portions 10 that are formed curved inwardly in the width direction, and the diaper 1 is a substantially hourglass shape overall.

For the surface sheet 2, for example, a fluid permeable plastic film or a nonwoven fabric is used.

The back face sheet 3 has an inner sheet 3a facing the surface sheet 2, an outer sheet 3b facing the inner sheet 3a, and both these sheets 3a, 3b are in substantially a same shape and same size to each other, and are joined by adhesion or welding. As the inner sheet 3a, a liquid impermeable plastic film or a nonwoven fabric is used, and as the outer sheet 3b, an air-permeable nonwoven fabric is used.

Each of the end edge portion flaps 11 of the front and back torso areas 1a, 1c are joined with a torso elastic member 16 in a stretched state placed between the surface sheet 2 and the back face sheet 3.

Further, the crotch area 1b and its proximity is provided with a front elastic strip member 21 and a back elastic strip member 22 across and along a width direction of the diaper 1. As these elastic strip members 21, 22, for example, nonwoven fabric having stretchability or strip shaped rubber and the like is used. These elastic strip members 21, 22 each extend in a width direction in a predetermined meander pattern that is curved in a convex shape toward a center line CL that divides the diaper 1 substantially in half to the front and back in the longitudinal direction, and the elastic strip members 21, 22 are provided in between the inner sheet 3a and the outer sheet 3b that structure the back face sheet 3 and, for example, are joined to an inner face of the outer sheet 3b in a stretched state. These front and back elastic strip members 21, 22 cooperate to give elasticity to the around-leg concave portions 10.

Note that, here, a sine curve is illustrated as an example as the meander pattern of these elastic strip members 21, 22, but the meander pattern can be appropriately changed so that the around-leg convex portions 10 can effectively fit around the leg of the wearer of the diaper.

Figure 3:
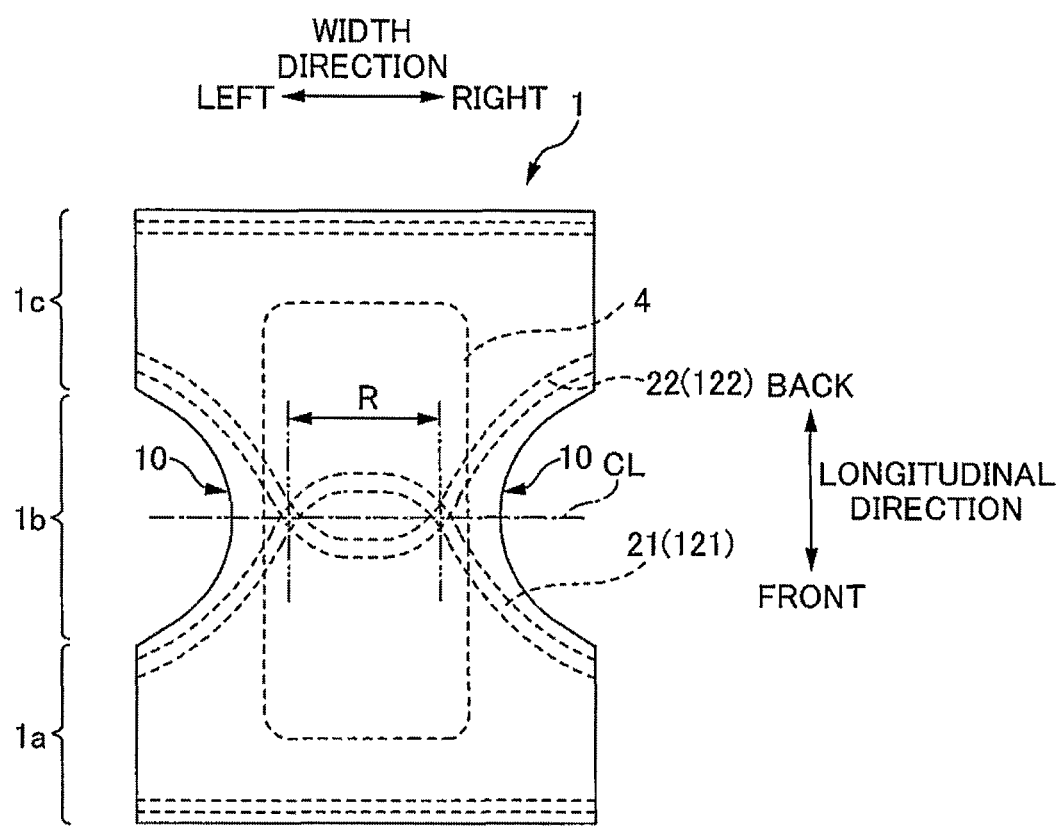
FIG. 3 is a perspective view of the diaper 1 with elastic strip members 21, 22 arranged so as to intersect with each other at a returning portion of each meander pattern.

Further, in order to increase fitting around substantially the entire length of the around-leg concave portion 10, as shown in FIG. 3, the elastic strip members 21, 22 may be arranged to intersect each other at the returning portion of each meander pattern, and further in order to weaken the elasticity in the intersecting region R, a portion of the elastic strip members 21, 22 belonging to the intersecting region R can be divided. Incidentally, elasticity of this intersected region R is weakened because if there is elasticity at the absorbent body 4 portion, creases are formed in the absorbent body 4, and there is fear that fluid absorption performance may deteriorate.

Manufacturing Method and Manufacturing Apparatus 30 of Composite Sheet of this Embodiment Such a diaper 1 is to be completed by a base material of the diaper 1 that is continuously flowing in the manufacturing line being joined and the like with various structural components. The manufacturing method and the manufacturing apparatus 30 of the composite sheet according to this embodiment carry out one of the processes. That is, here the manufacturing method and the manufacturing apparatus 30 are applied in a process of attaching in the above-described meander pattern a continuous body of an elastic strip member 121 to be the above-described front elastic strip member 21 (corresponds to a continuous body of a first elastic strip member, herein also referred to as a first elastic strip member 121) and a continuous body of an elastic strip member 122 to be the above-described back elastic strip member 21 (corresponds to a continuous body of a second elastic strip member, herein also referred to as a second elastic strip member 122) to a continuous body of a sheet 103b to be an outer sheet 3b of the above-described back face sheet 3 (herein referred to as a sheet 103b).

Figure 4A:
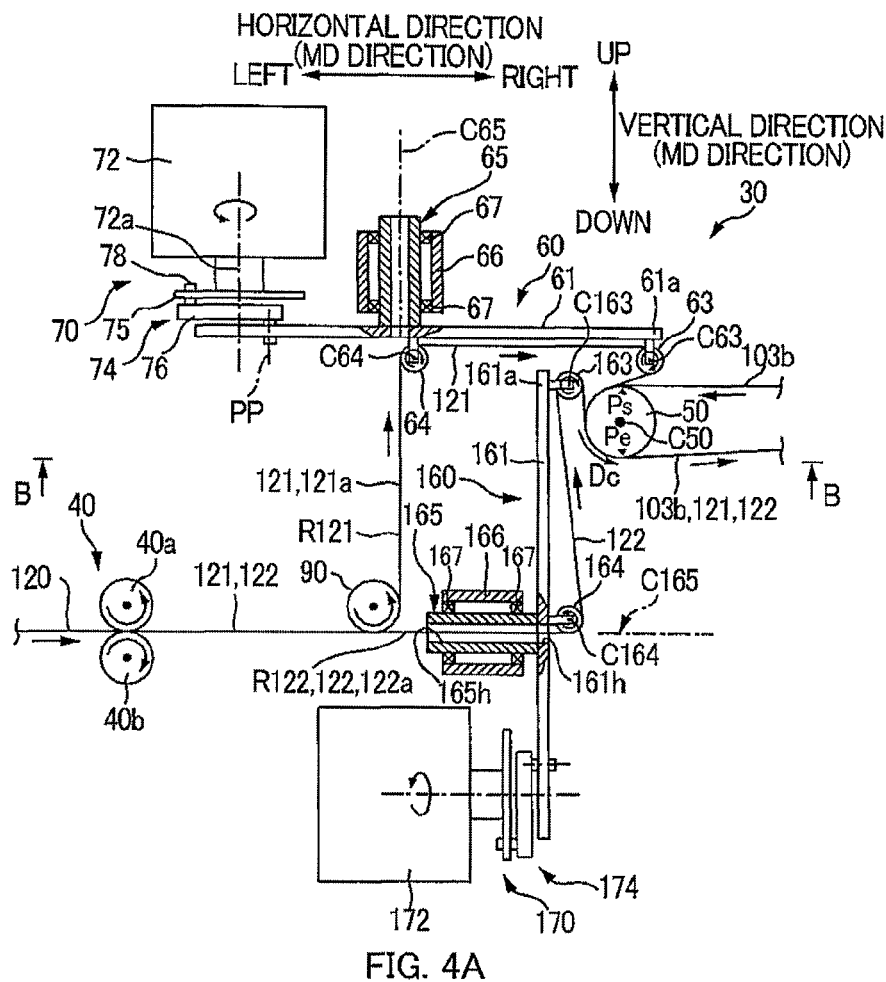
FIG. 4A is a perspective view showing a partially cutaway manufacturing apparatus 30 of this embodiment.
Figure 4B:
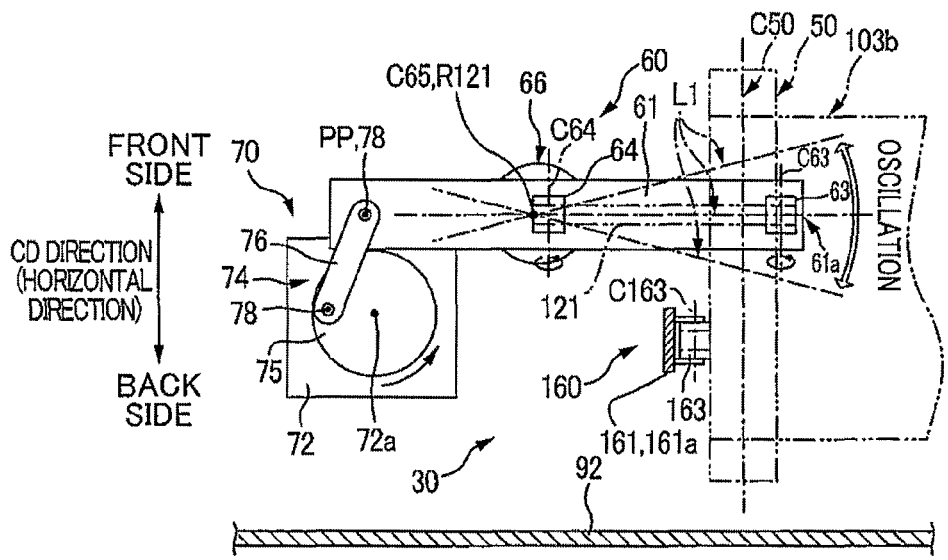
FIG. 4B is a cross-sectional view taken along B-B in FIG. 4A.
Figure 5:
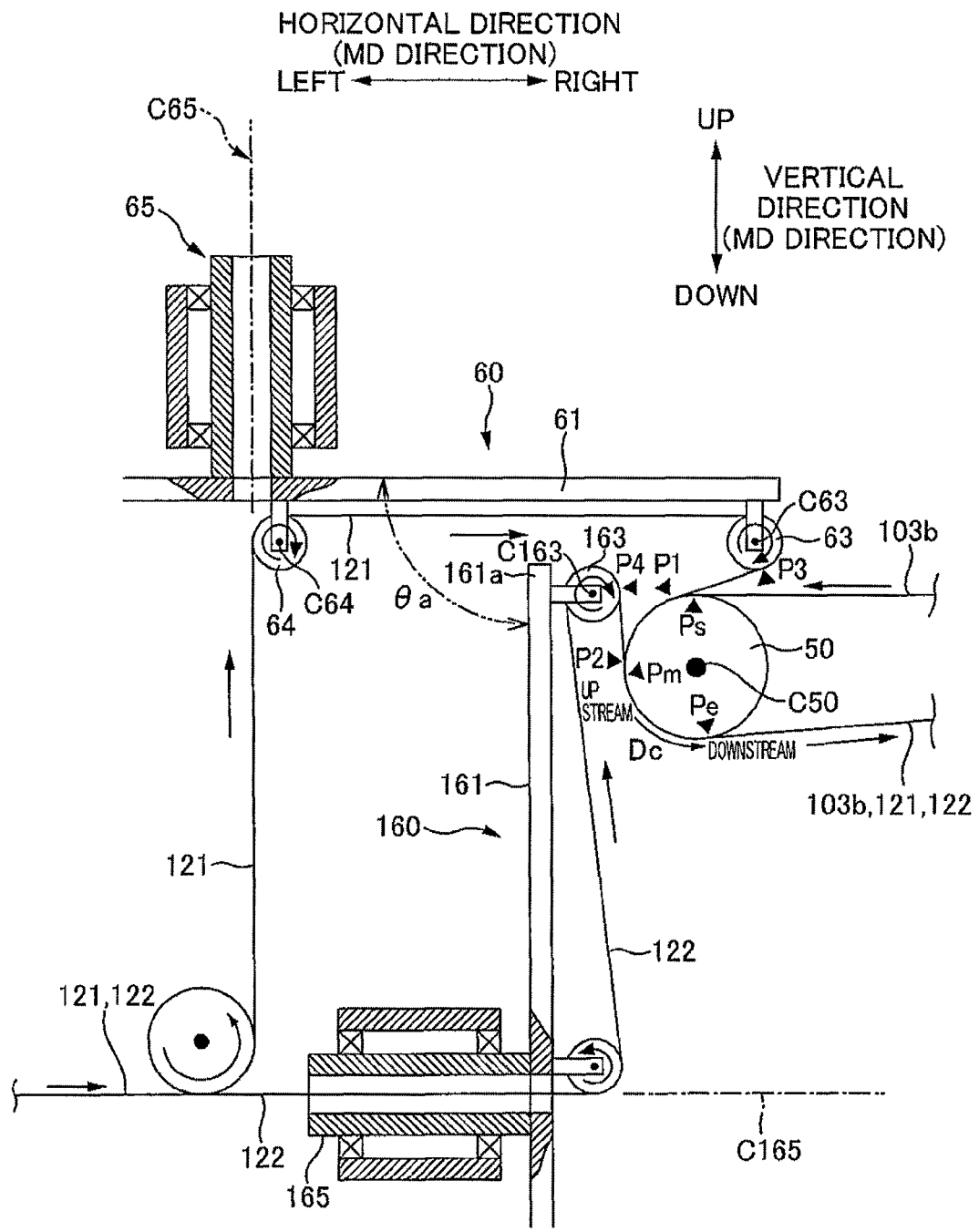
FIG. 5 is an enlarged view of a portion close to a transporting roll 50 in FIG. 4A.

FIG. 4A is a perspective view showing a partially cutaway manufacturing apparatus 30 of this process, and FIG. 4B is a cross-sectional view taken along B-B in FIG. 4A. Further, FIG. 5 is an enlarged view in the vicinity of the transport roll 50 in FIG. 4A.

Note that, hereinbelow, a width direction of the manufacturing apparatus 30 is referred to as a CD direction or front side-back side. Further, a direction that is perpendicular to the CD direction is referred to as an MD direction. That is, the MD direction is an arbitrary direction in a plane that is perpendicular to the CD direction. Further, regarding the MD direction, as shown in FIG. 4A, the two direction that are perpendicular to each other are defined as an up-down direction (vertical direction) and a left-right direction (horizontal direction). Incidentally, as shown in FIG. 4B, the CD direction is also in a horizontal direction, and is in a perpendicular relation to the left-right direction in the horizontal direction.

This manufacturing apparatus 30 includes (1) a transporting roll 50 that transports the sheet 103b in the MD direction (corresponds to the transporting direction) by wrapping the sheet 103b around in a predetermined wrapping angle and rotating, (2) a slitting apparatus 40 arranged to a left side of the transporting roll 50 and that divides in two in the center in the CD direction a sheet member 120, that is an original sheet made of an elastic strip member that is sent continuously from the left, and forms first and second elastic strip members 121, 122, (3) a first guide member 60 that continuously places the first elastic strip member 121 in a stretched state to a portion of the sheet 103b that is wrapped around an outer circumferential face of the transporting roll 50 and joins them, and (4) a second guide member 160 that continuously places the second elastic strip member 122 in a stretched state to a portion of the same sheet 103b and joins them.

These first and second guide members 60, 160 each feed the elastic strip members 121, 122 that they are in charge of toward the sheet 103b in the MD direction and reciprocates each of the elastic strip members 121, 122 in the CD direction (corresponds to an intersecting direction). Thus, each of the elastic strip members 121, 122 are overlapped on the sheet face of the sheet 103b and joined while the joining position to the sheet 103b in the CD direction is changed every moment continuously. As a result, the sheet face of the sheet 103b is attached in a surface-contact state with a pair of the elastic strip members 121, 122 in an intended meander pattern such as a since curve.

Incidentally, it is needless to say that before joining each of the elastic strip members 121, 122 to the sheet 103b, a hot-melt adhesive and the like is to be applied to each of the elastic strip members 121, 122 by an adhesive applying apparatus that is not shown.

Hereinbelow, each structural element 40, 50, 60, 160 is described. Note that, in the below description, unless specifically stated, each structural device according to the manufacturing apparatus 30 is cantilevered via an appropriate bracket that is not shown by a vertical support wall 92 (namely a panel) that extends along an entire length of the manufacturing apparatus 30 in the MD direction. That is, as shown in FIG. 4B, at a back side in the CD direction (a back side of a plane of paper in FIG. 4A) is provided the support wall 92 along a direction substantially parallel to the MD direction (a direction substantially parallel to the plane of paper). A vertical wall face of this support wall 92 supports portions at the back side in the CD direction of each structural device, and portions at the front side are in a not supported state.

(1) Transporting Roll 50

The transporting roll 50 has a cylindrical body with a rotational axis C50 in the horizontal CD direction as a main body, and rotates anti-clockwise in a predetermined peripheral speed in a direction along the MD direction as a circumferential direction Dc. This transporting roll 50 is supplied with the sheet 103b from the right substantially horizontally, for example. With an approximately 12 o'clock position at an upper portion of the transporting roll 50 as a wrap around starting position Ps, the sheet 103b is wrapped around an outer circumferential face of the transporting roll 50, from the position Ps at a wrap around angle of, for example, 180° to 200°, and its transporting direction is reversed. Ultimately, the sheet 103b is fed to the right in the substantially horizontal direction, with an approximately 6 o'clock position at a lower portion of the transporting roll 50 as a wrap around finishing position Pe.

This transporting roll 50 may be structured as a drive roll that rotatingly drives with an appropriate motor and the like as a driving source, or may be structured as a follower roll that is rotatingly driven by the sheet 103b.

(2) Slitting Apparatus 40

A slitting apparatus 40 has a top and bottom pair of discal rotating blades 40a, 40b in the center in the CD direction. When passing these rotating blades 40a, 40b, the sheet member 120 that is an original plate of the elastic strip members 121, 122 is divided in half, and thereby a pair of the elastic strip members 121, 122, namely the first elastic strip member 121 and the second elastic strip member 122, is produced. The first elastic strip member 121 is fed to a first guide member 60 and the second elastic strip member 122 is fed to a second guide member 160.

(3) First Guide Member 60

The first guide member 60 has a tabular first oscillating arm 61 provided above the transporting roll 50. The first oscillating arm 61 has a longitudinal direction and, with the longitudinal direction to the left and right in the horizontal direction, is arranged so as to cross over the rotational axis C50 of the transporting roll 50 left and right in the horizontal direction.

Then, with a spindle portion 65 (hereafter also referred to as a first spindle portion 65) positioned to the left than the rotational axis C50 as a swivel fulcrum, the oscillating end 61a positioned to the right than the rotational axis C50 can be made to oscillate in the CD direction.

Further, the first spindle portion 65 is, for example, a shaft body 65 that protrudes integrally and upwards from a top surface of the first oscillating arm 61, and is rotatably supported inside an outer cylindrical member 66 via bearings 67. The outer cylindrical member 66 is fixed to the support wall 92 via an appropriate bracket that is not shown, and thus the first oscillating arm 61 is supported to be able to swivel around a vertical rotational central axis C65 of the first spindle portion 65.

Further, a drive mechanism 70 of the first oscillating arm 61 is a motor 72 combined with a crank mechanism 74. A crank mechanism 74 has on a drive rotating axis 72a of the motor 72 in an up-down direction in the MD direction a circular disk member 75 that has been fixed integrally and concentrically and a rod-shaped link member 76 that connects the disk member 75 and a power point PP of the first oscillating arm 61. Then, a position eccentric from a drive rotating axis 72a in the disk member 75 is connected with an end portion of the link member 76 by a coupling pin 78 or the like. Thus, every time the disk member 75 rotates once, the link member 76 is reciprocated once only in its longitudinal direction, and the first oscillating arm 61 performs an oscillating movement only once by this one reciprocating movement.

On a lower surface which is a surface to a side opposing the transporting roll 50 of the first oscillating arm 61 is rotatably supported a pair of rollers 63, 64 around each of the horizontal rotational axes C63, C64. One roller 63 is a first oscillating end side roller 63 provided to an oscillating end 61a, and the other roller 64 is a first spindle portion side roller 64 provided to a position closer to the first spindle portion 65 than the first oscillating end side roller 63.

Thus, the first elastic strip member 121 of the elastic strip members 121, 122 that is fed from the above-described slitting apparatus 40 is first fed from the left to the right along the horizontal direction, the travel direction is changed upwards in the vertical direction with the reversal roller 90 at a position that matches a plane position of the rotational central axis C65 of the first spindle portion 65 of the first oscillating arm 61, and the first elastic strip member 121 reaches the first spindle portion side roller 64 and is put around the outer circumferential face of the first spindle portion side roller 64. Then, with the roller 64, the first elastic strip member 121 is guided to the oscillating end 61a that is to the right than transporting roll 50, thereafter wrapped around the outer circumferential face of the first oscillating end side roller 63 at the oscillating end 61a, and after being reversed in the travel direction substantially to the left by the wrapping, is placed in the wraparound range Ps-Pe of the sheet 103b from the upper right of the transporting roll 50.

Then, during the above placing, the first oscillating end side roller 63 reciprocates in the CD direction due to the oscillating movement of the oscillating end 61a, thus the first elastic strip member 121 is joined to a sheet face of the sheet 103b in a desired meander pattern with its joining position in the sheet face of the sheet 103b being continuously changed in the CD direction. Further, at the time of this placing, the first elastic strip member 121 is restrained in a substantially flat shape by wrapping around the outer circumferential face of the first spindle portion side roller 64 and an outer circumferential face of the first oscillating end side roller 63, so that the first elastic strip member 121 is joined to the sheet 103b in a surface-contact state (corresponds to a "first joining").

Here, preferably, as shown in FIG. 5, the position P1 (hereafter, also referred to as first placing position P1) at which the first elastic strip member 121 is placed on the sheet 103b with the first oscillating arm 61 is set in a region to an upstream side than a middle position Pm in the circumferential direction Dc in the above wraparound range Ps-Pe. With this setting, the region to overlap and press against the first elastic strip member 121 on the sheet 103b of the transporting roll 50 can be widely ensured along the circumferential direction Dc, and as a result, the first elastic strip member 121 can be strongly joined to the sheet 103b. Note that, to elaborate on the above-described first placing position P1, the first placing position P1 refers to a position where the first elastic strip member 121 fed from the first oscillating end side roller 63 of the first oscillating arm 61 first contacts the sheet 103b.

By the way, as shown in FIG. 4B, each of the first oscillating end side roller 63 and the first spindle portion side roller 64 is arranged on a line L1 connecting the oscillating end 61a and the rotational central axis C65 of the first spindle portion 65. Further, the first oscillating end side roller 63 is fixed to the first oscillating arm 61 so that its direction to the first oscillating arm 61 is unchangeable, in a state the outer circumferential face is facing the rotational central axis C65 of the first spindle portion 65, while, the first spindle portion side roller 64 is also fixed to the first oscillating arm 61, so that its direction to the arm 61 is unchangeable, in a state the outer circumferential face of the roller 64 is facing the oscillating end 61a of the first oscillating arm 61.

Thus, with this configuration, in accordance with the reciprocating movement of the first oscillating end side roller 63, the outer circumferential face of the first spindle portion side roller 64 is always facing the first oscillating end side roller 63, thus, the first elastic strip member 121 can be certainly fed toward the first oscillating end side roller 63. As a result, the falling off of the first elastic strip member 121 from the first oscillating end side roller 63 can be effectively prevented and the like, and stability of the travel state of the first elastic strip member 121 can be achieved.

Further, in accordance with the above configuration, the rotational axis C63 of the first oscillating end side roller 63 and the rotational axis C64 of the first spindle portion side roller 64 are always maintained in a parallel state, regardless of the oscillation movement of the first oscillating arm 61. Thus, a tension difference to both end edges in the width direction of the first elastic strip member 121 that may occur with the oscillation movement of the first oscillating arm 61 can be certainly eased, and as a result, the first elastic strip member 121 falling off from the first oscillating end side roller 63 or the first spindle portion side roller 64 can be effectively prevented.

To further stabilize the travel state, as shown in, FIG. 4A, the supply route R121 (hereafter, also referred to as first supply route R121) of the first elastic strip member 121 to the first spindle portion side roller 64 is aligned in a straight line with the rotational central axis C65 of the first spindle portion 65, and the roller 64 is arranged so that the outer circumferential face of the first spindle portion side roller 64 is in contact with the rotational central axis C65 of the first spindle portion 65. Thus, the movement of the first elastic strip member 121 in the CD direction that may occur with the oscillation movement of the first oscillating arm 61 mainly appears as a twist in the portion 121a of the first elastic strip member 121 to the upstream side than the first spindle portion side roller 64 and is absorbed therein, and as a result, the falling off of the first elastic strip member 121 from the roller 64 can be effectively prevented.

Further, as described above, the outer circumferential face of the first spindle portion side roller 64 is in contact with the rotational central axis C65 of the first spindle portion 65, so that the movement amount in the CD direction of the roller 64 that may occur with the oscillation movement of the first oscillating arm 61 can be made to substantially zero, and also with this, the falling off of the first elastic strip member 121 from the first spindle portion side roller 64 can be effectively prevented.

(4) The Second Guide Member 160

The second guide member 160 is a member with roughly the same structure as the above-described first guide member 60. As shown in FIG. 4B, the second guide member 160 is arranged more to the back side than the first guide member 60 in the CD direction. Thus, the second elastic strip member 122, that this second guide member 160 is in charge of, is attached more to the back side in the CD direction than the first elastic strip member 121 and in parallel thereto, the elastic strip member 121 being attached to the sheet 103b by the first guide member 60.

Figure 1B:
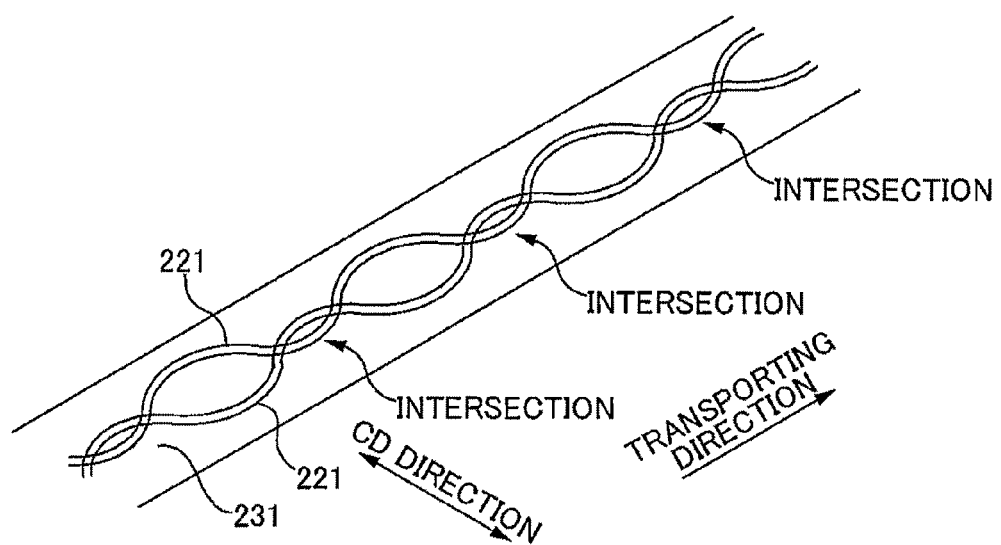
FIG. 1B is an explanatory view of another arrangement pattern of the elastic strip member 221.

However, depending on the disposable diaper 1, as shown in FIG. 3 (or FIG. 1B), an arrangement pattern of the first and the second elastic strip members 121, 122 in which the first elastic strip member 121 (221) and the second elastic strip member 122 (221) are partially overlapped is possible. In that case, if the first oscillating arm 61 and the second oscillating arm 161 are arranged in parallel, these oscillating arms 61, 161 will come in collision with each other and cannot form the above-described pattern.

In this embodiment, in order to avoid the above collision, as shown in FIG. 4A, the position of the second oscillating arm 161 in a circumferential direction Dc of the transporting roll 50 is made different from that of the first oscillating arm 61. That is, the second oscillating arm 161 is arranged displaced to a downstream side in the circumferential direction Dc than the first oscillating arm 61. In accordance with this, as shown in FIG. 5, a second placing position P2 where the second oscillating arm 161 places the second elastic strip member 122 on the sheet 103b is positioned more to a downstream side in the circumferential direction Dc than the first placing position P1 of the first oscillating arm 61. Thus, interference between the first and the second elastic strip members 121, 122 in the placing positions P1, P2 can also be avoided. Incidentally, the above-described second placing position P2 refers to a position that, as similar to the definition of the first placing position P1, the second elastic strip member 122 that has been fed from the second oscillating end side roller 163 of the second oscillating arm 161 first contacts the sheet 103b.

Hereafter, a structure of the second guide member 160 is described in detail.

As shown in FIG. 5, the second oscillating arm 161 is at a position in which the first oscillating arm 61 is rotatingly moved to a downstream side in the circumferential direction Dc for a predetermined rotating angle θa only around an imaginary axis, that is not shown, parallel to the rotational axis C50 of the transporting roll 50, the rotating angle θa being 90° in the shown example.

With this 90° rotational movement, the second oscillating arm 161 is arranged to the left of the first oscillating arm 61 and the transporting roll 50, and further the second oscillating arm 161 is arranged crossing over the rotational axis C50 of the transporting roll 50 vertically in the vertical direction, with its longitudinal direction in the vertical direction. With the second spindle portion 165 that is positioned lower than the rotational axis C50 as a swivel fulcrum, the oscillating end 161a positioned above the rotational axis C50 is structured so as to be able to oscillate in the CD direction.

As shown in FIG. 4, the driving mechanism 170 for the oscillating movement is the motor 172 combined with the crank mechanism 174, as in the case for the first guide member 60. Further, the second spindle 165 is a shaft body 165 that extends integrally and to the left from a left surface of the second oscillating arm 161, as similar to the case with the first guide member 60, and this shaft body 165 is supported rotatably in an outer cylindrical member 166 via the bearings 167. Note that, the outer cylindrical member 166 is fixed to the support wall 92.

Here, the second spindle portion 165 is formed with a through hole 165h along its rotational central axis C165 direction, and corresponding to the through hole 165h the second oscillating arm 161 is also formed with a through hole 161h in the left to right direction. These through holes 165h, 61h serve as a supply route R122 to the second oscillating arm 161 of the second elastic strip member 122 to be described later.

Further, on a right side surface of the second oscillating arm 161 which is a surface on a side opposing the transporting roll 50, each of a pair of rollers 163, 164 is rotatably supported around substantially horizontal rotating axes C163, C164. One roller 163 is a second oscillating end side roller 163 provided at an oscillating end 161a, and another roller 164 is a second spindle portion side roller 164 provided more to the second spindle portion 165 than the second oscillating end side roller 163.

Therefore, the second elastic strip member 122 that is fed from the slitter apparatus 40 is fed from the left to the right in the horizontal direction, while being in parallel in the CD direction next to the first elastic strip member 121 that is to be sent to the above-described first guide member 60. Then, the elastic strip member 122 passes through the through hole 65h in the second spindle portion 165 and exits in a surface to the right side of the second oscillating arm 161. Then, by being put around the outer circumferential face of the second spindle portion side roller 164 installed on the same surface, the elastic strip member 122 is guided to the above oscillating end 161a, and thereafter, wrapped around the outer circumferential surface of the second oscillating end side roller 163 at the oscillating end 161a and after the travel direction is reversed substantially downwards with the wrapping, the elastic strip member 122 is placed in the wraparound range Ps to Pe of the sheet 103b from the upper left of the transporting roll 50.

Then, during the above placing, the second oscillating end side roller 163 reciprocates in the CD direction due to the oscillating movement of the oscillating end 161a, thus the second elastic strip member 122 is joined to a sheet face of the sheet 103b in a desired meander pattern with its joining position in the sheet face of the sheet 103b being continuously changed in the CD direction. Further, at the time of this placing, the second elastic strip member 122 is restrained in a substantially flat shape by wrapping around the outer circumferential face of the second spindle portion side roller 164 and an outer circumferential face of the second oscillating end side roller 163, so that the elastic strip member 122 is joined to the sheet 103b in a surface-contact state (corresponds to a "second joining").

Here, preferably, similar to the case of the first placing position P1 of the first elastic strip member 121, the second placing position P2 of the second elastic strip member 122 is set in a region to the upstream side than a middle position Pm of the circumferential direction Dc within the above wraparound range Ps-Pe (refer to FIG. 5). If the second placing position P2 is set in this way, a region of the transporting roll 50 to overlap the second elastic strip member 122 on the sheet 103b and to press it against thereto can be obtained widely along the circumferential direction Dc, and as a result, the second elastic strip member 122 can be strongly joined to the sheet 103b.

Further, the above-described rotating angle θa (refer to FIG. 5), namely, the rotating angle θa of the positional relationship between the first oscillating arm 61 and the second oscillating arm 161 is preferably selected from an angle excluding 0° and 360°, more preferably, is selected from a range of 30°-150°, further more preferably selected from a range of 45°-135°, and even more preferably selected from a range of 0°-110°.

If P2 is set to an arbitrary value in these ranges, while arranging both the first oscillating end side roller 63 and the second oscillating end side roller 163 close to the transporting roll 50, a space occupied by the manufacturing apparatus 30 can be made small.

Figure 6:
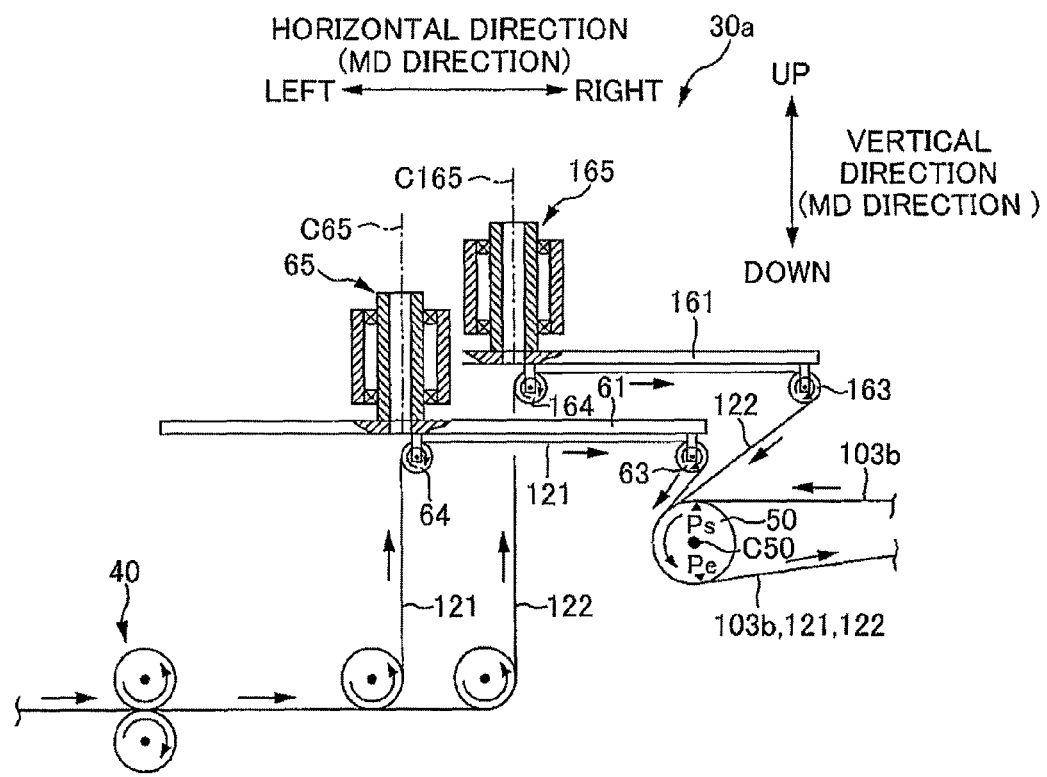
FIG. 6 is an explanatory view of another relative positional relationship of a first oscillating arm 61 and a second oscillating arm 161.
Figure 7:
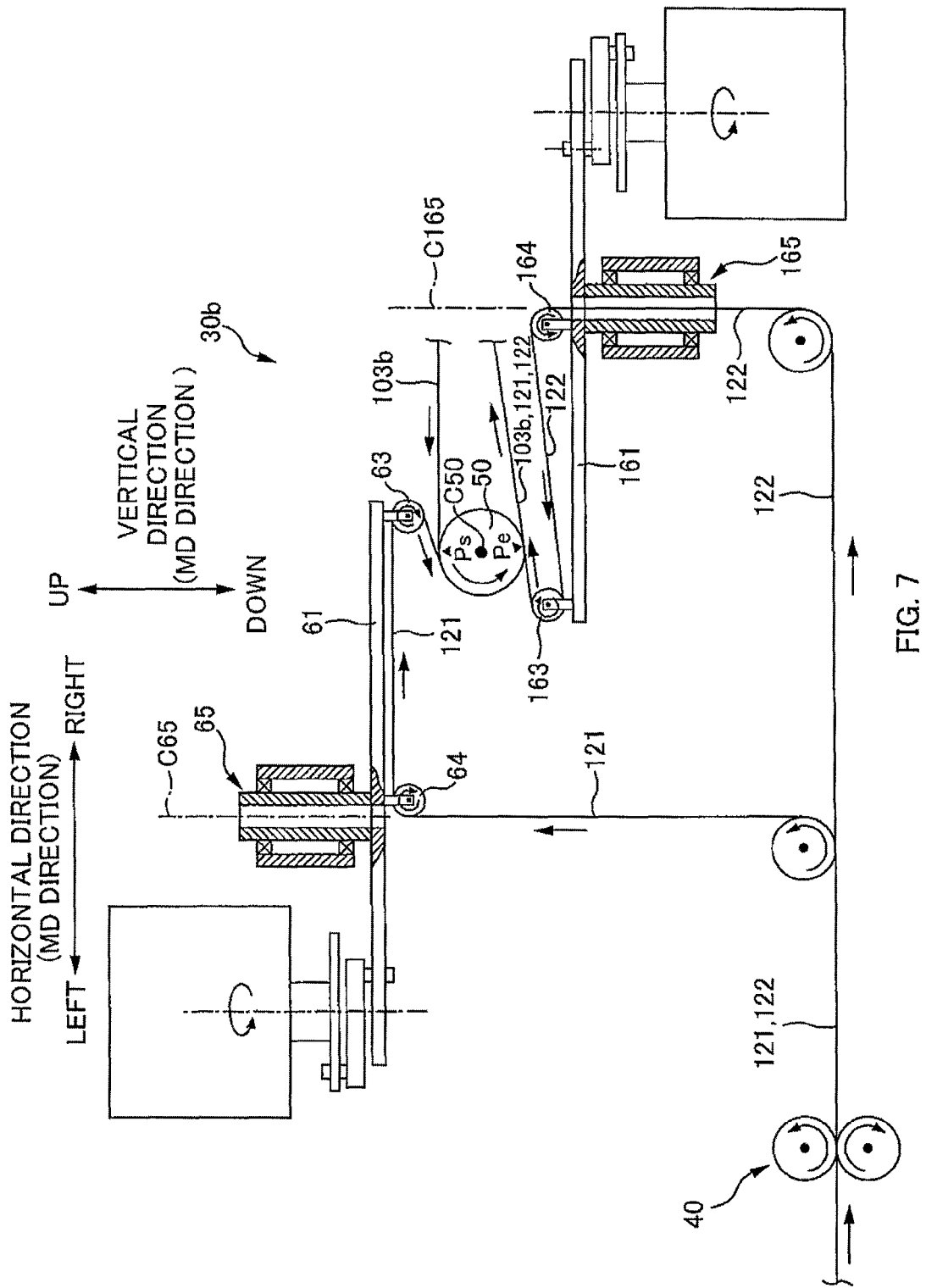
FIG. 7 is an explanatory view of yet another relative positional relationship of the first oscillating arm 61 and the second oscillating arm 161.

For example, in the case where the rotational angle does not correspond to the above-described range, that is in the case the rotating angle θa is 0°, as shown in FIG. 6, the configuration of the manufacturing apparatus 30a is compact but the second oscillating end side roller 163 cannot be arranged close to the transporting roll 50. Further, also in the case of FIG. 7 where the rotational angle does not correspond to the range, that is, in the case where the rotating angle θa is 180°, both the first and the second oscillating end side rollers 63, 163 can be arranged close to the transporting roll 50 but the configuration of the manufacturing apparatus 30b becomes large. That is, in either of the examples in FIGS. 6 and 7, the close arrangement of the oscillating end side rollers 63, 163 and making the manufacturing apparatus 30 compact cannot be both successfully achieved.

Figure 8:
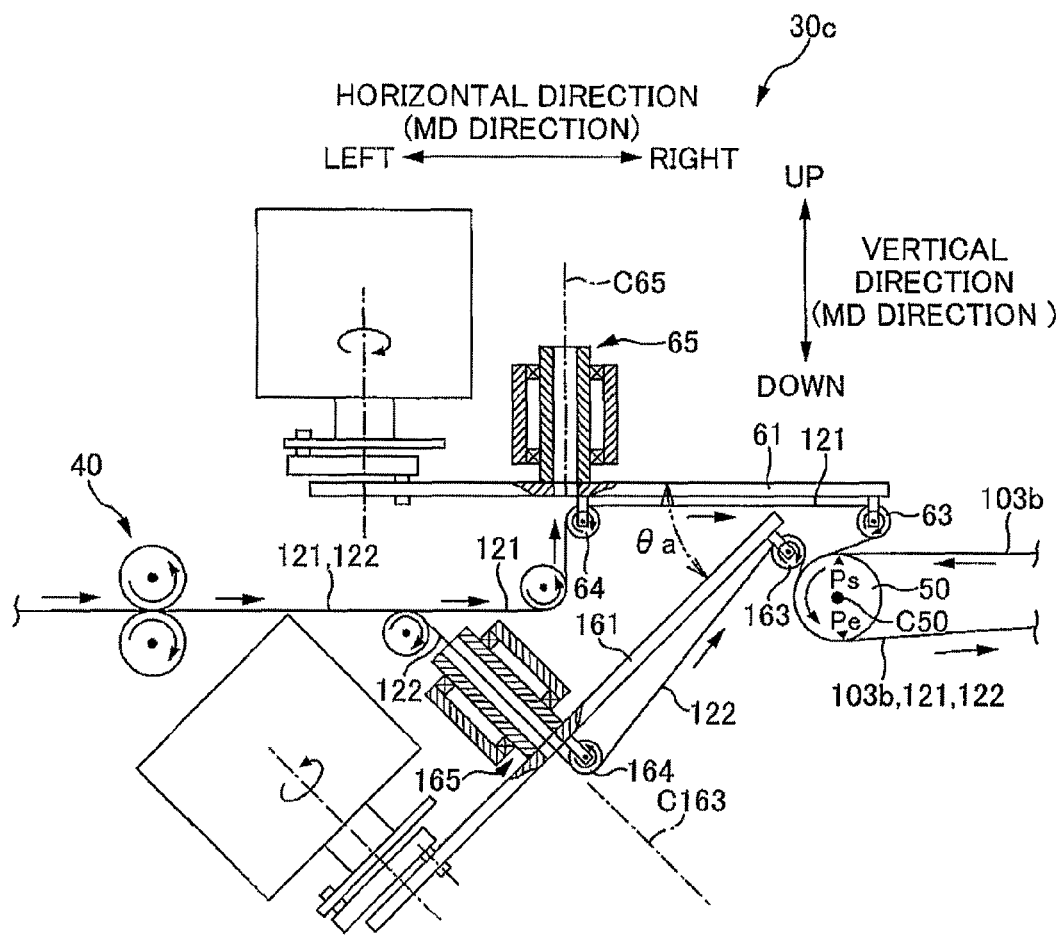
FIG. 8 is an explanatory view of further another relative positional relationship of the first oscillating arm 61 and the second oscillating arm 161.

In contrast to this, in the case where the rotating angle θa is 90° as in FIG. 4A and the rotating angle is in a preferable range of the above-described rotating angle θa, and in the case where the rotating angle θa is 45° as in FIG. 8, both the first and the second oscillating end side rollers 63, 163 can be arranged close to the transporting roll 50, and the manufacturing apparatuses 30, 30c can be made compact. That is, the close arrangement of the oscillating end side rollers 63, 163 and making the manufacturing apparatus 30 compact can be both successfully achieved.

By the way, the reason that each of the oscillating end side rollers 63, 163 should be closely arranged to the transporting roll 50 is because if they are not closely arranged, the following property of the oscillating movements of each of the elastic strip members 121, 122 in respect to the oscillating movements of each of the oscillating arms 61, 161 deteriorates. Namely, in the case the rollers are not closely arranged, a portion of each of the elastic strip members 121, 122 cast loose toward the sheet 103b from each of the oscillating end side rollers 63, 163, bends like a whip when reversing the oscillating movement, and a movement delay from each of the oscillating end side rollers 63, 163 becomes large, and as a result the actual joining position of the sheet 103b becomes easily displaced from a target joining position of each of the elastic strip members 121, 122.

Note that, a guideline of the close arrangement is exemplified below. That is, as shown in FIG. 5, there is exemplified that a distance between a position P3 (P4) at which the elastic strip member 121 (122) comes apart from the outer circumferential face of the oscillating end side roller 63 (163) and a position P1 (P2) at which the elastic strip member 121 (122) that has been cast loose from the position P3 contacts the transporting roll 50 is made greater than 30 mm and smaller than 80 mm, in a state where the line L1 of the oscillating arm 61 (161) is facing a direction parallel to the MD direction.

By the way, the above described relative positional relationship of the second oscillating arm 161 in respect to the first oscillating arm 61 can be expressed as follows.

The rotational central axis C65 of the first spindle portion 65 of the first oscillating arm 61 and the rotational central axis C165 of the second spindle portion 165 of the second oscillating arm 161 are facing a direction intersecting each other in an imaginary plane (a plane parallel to a paper plane of FIG. 4A or FIG. 5) that has the rotational axis C50 direction of the transporting roll 50 as the direction of the normal, and the second oscillating arm 161 is arranged in respect to the first oscillating arm 61 so that the intersecting angle θb of the rotational central axis C65 and the rotational central axis C165 becomes 90°.

Here, as a preferable range of the intersecting angle θb, angles excluding 0° and 360° are given, more preferably a range of 30°-150° is given, further more preferably a range of 45°-135° is given, and even further more preferably a range of 80°-110° is given. Then, if the angle is set to an arbitrary value within these ranges, as described above, the close arrangement of the oscillating end side rollers 63, 163 and making the manufacturing apparatus 30 compact can be both successfully achieved. Incidentally, the configuration example in FIG. 6 corresponds to a case where the above-described intersecting angle θb is 0° or 360°, the configuration example in FIG. 7 corresponds to a case where the intersecting angle θb is 180°, the configuration example in FIG. 8 corresponds to the case where the angle is 45°, and the configuration example in FIG. 4A corresponds to a case where the angle is 90°.

The configuration of the second guide member 160 has been described above, and the structure shown in below (a) to (c) are all the same as those for the first guide member 60, and therefore their detailed description is omitted.

(a) Each of the second oscillating end side roller 163 and the second spindle portion side roller 164 are arranged on a straight line that connects the oscillating end 161a of the second oscillating arm 161 and the rotational central axis C165 of the second spindle portion 165.

(b) The second oscillating end side roller 163 is fixed to the second oscillating arm 161 so that its outer circumferential face is facing toward the rotational central axis C165 of the second spindle portion 165 of the second oscillating arm 161 with its orientation in respect to the second oscillating arm 161 being unable to be changed and the second spindle portion side roller 164 is also fixed to the second oscillating arm 161 so that its outer circumferential face is facing toward the oscillating end 161a of the second oscillating arm 161 with its orientation in respect to the second oscillating arm 161 being unable to be changed.

(c) The supply route 8122 of the second elastic strip member 122 to the second spindle portion side roller 164 is aligned in one line with the rotational central axis C165 of the second spindle portion 165, and the second spindle portion side roller 164 is arranged so that the circumferential face of the second spindle portion side roller 164 is contacting the rotational central axis C165 of the second spindle portion 165.

Other Embodiments

The embodiments of the present invention have been described above, but the present invention is not limited to these embodiments, and below modifications are possible.

Figure 9:
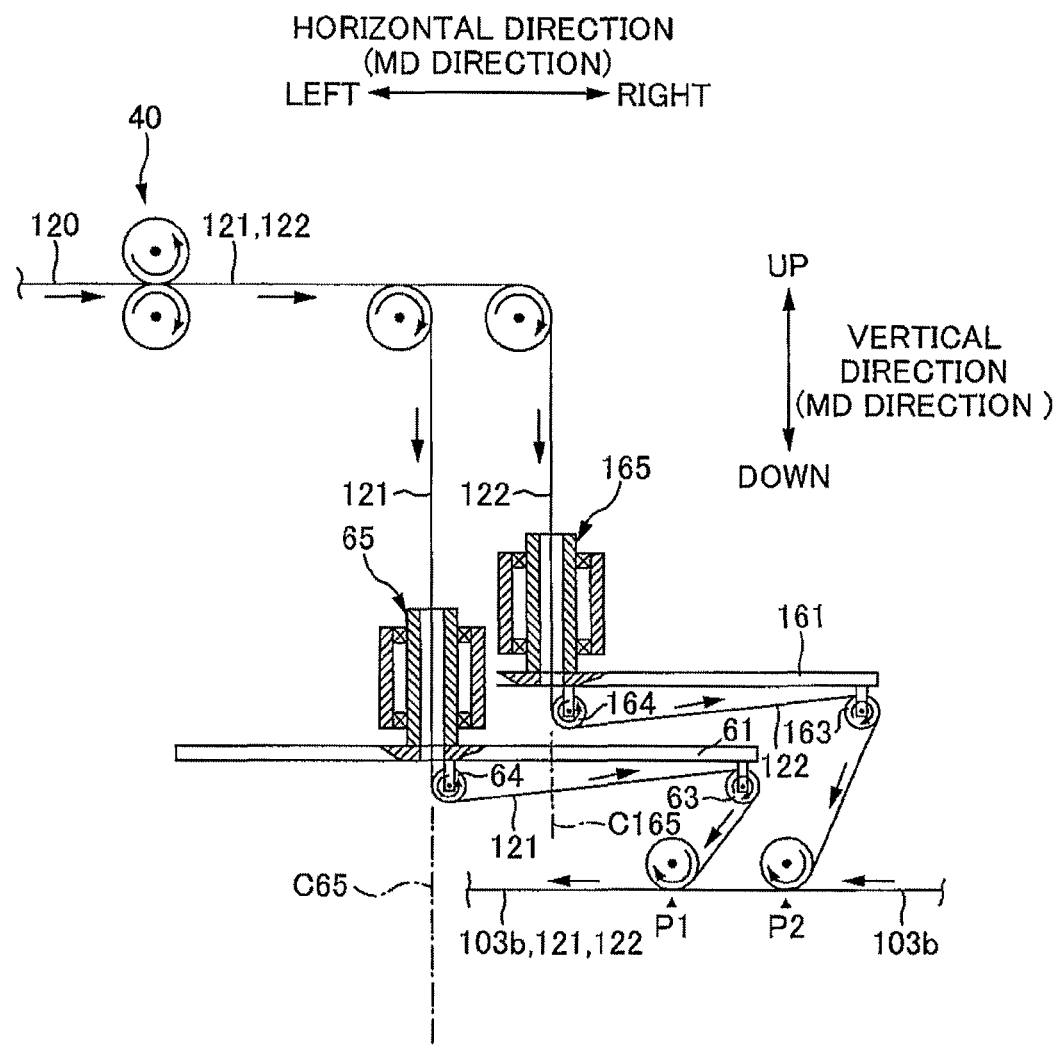
FIG. 9 is an explanatory diagram showing another embodiment of manufacturing apparatus according to this invention.

In the above-described embodiment, the sheet 103b is wrapped around the transporting roll 50 at a predetermined wraparound angle and transported, and the first elastic strip member 121 and the second elastic strip member 122 are placed to a portion of the sheet 103b that has been wrapped and joined, but it is not limited thereto. For example, as shown in FIG. 9, the sheet 103b does not have to be wrapped around the transporting roll 50 at each of the placing positions P1, P2 of each of the elastic strip members 121, 122. That is, as in the illustrated example the first and the second placing positions P1, P2 can be set in the transporting path of the linear sheet 103b along the horizontal direction.

In the above-described embodiment, the two oscillating arms 61, 161 are set, but the number of the oscillating arms merely has to be a multiple, namely the number can be equal to or greater than three.

In the above-described embodiment, the manufacturing step of the pants type diaper 1 is illustrated, but it is not limited thereto and the invention may be applied for manufacturing of expanding type diapers (a type of diaper in which the front torso area 1a and the back torso area 1c are held fixed by a tape fastener when wearing).

In the above-described embodiment, there is illustrated a structure in which an oscillating arm 61 (161) has two rollers of an oscillating end side roller 63 (163) and a spindle portion side roller 64 (164), but it is not limited thereto, and one roller may be provided in between the oscillating end side roller 63 (163) and the spindle portion side roller 64 (164). Note that, in this case the rotating axis of the roller to be additionally provided may be in parallel to the rotational axis C64 (C164) of the spindle portion side roller 64 (164).

In the above-described embodiment, as shown in FIG. 4A, the rotational central axis C65 of the first spindle portion 65 of the first guide member 60 is oriented in the up-down direction (vertical direction), the rotational central axis C165 of the spindle portion 165 of the second guide member 160 is oriented in the left-right direction (horizontal direction), and the rotational axis C50 of the transporting roll 50 is oriented in the CD direction (horizontal direction). However, it is not limited thereto, as long as the rotational central axis C65 (C165) of the spindle portion 65 (165) of the first guide portion 60 or the second guide portion 160 and the rotational axis C50 of the transporting roll 50 are in a perpendicular relationship with each other.

In the above-described embodiment, the rotational axis C63 (C163) of the oscillating end side roller 63 (163) and the rotational axis C64 (C164) of the spindle portion side roller 64 (164) are in the substantially horizontal direction. The reason is to hand over the elastic strip member 121 (122) in a substantially flat shape with little torsion in respect to the transporting roll 50 with the rotational axis C50 in the horizontal direction that is the CD direction. Thus, the orientation of the rotational axes C63 (C163), C64 (C164) of the oscillating end side roller 63 (163) and the spindle portion side roller 64 (164) is not limited to a substantially horizontal direction in any way, and can be changed according to a direction in which the rotational axis C50 of the transporting roll 50 faces. That is, the rotational axis C63 (C163) of the oscillating end side roller 63 (163) and the rotational axis C64 (C164) of the spindle portion side roller 64 (164) may be arranged so that the face that the rotational axes C63 (C163), C64 (C164) make with the oscillating movement of the oscillating arm 61 (161) is to be parallel to the rotational axis C50 of the transporting roll 50. Furthermore, the oscillating end side roller 63 (163) and the spindle portion side roller 64 (164) may be arranged so that the rotational axes C63 (C163), C64 (C164) become perpendicular to the rotational central axis C65 (C165) of the spindle portion 65 (165) that is in a perpendicular relationship with the rotational axis C50 of the transporting roll 50.

In the above-described embodiment, a flat bone roll that has a circumferential face that is flat across the width direction (CD direction) of the roller is used as the oscillating end side roller 63 (163) and the spindle portion side roller 64 (164), but it is not limited thereto in any way. For example, a crowned roller may be used. This crowned roller refers to a roller with a largest diameter portion of the roller set in a central portion in the width direction. With this roller, the elastic strip member 121 (122) put around the outer circumferential face is given a centripetal force toward the central portion in the width direction of the roller by the largest diameter portion of the outer circumferential face so that it becomes difficult for the elastic strip member 121 (122) to fall off from the roller. As an example such a crowned roller, there may be, for example, such as a roller formed with annular ribs along a circumferential direction in only the central portion in the outer circumferential face, or a roller that has a radius that gradually increases from end portions toward the central portion of the outer circumferential face.

In the above-described embodiment, a hot-melt adhesive was applied with an adhesive applying apparatus to the elastic strip members 121, 122, but it is not limited thereto in any way as long as the sheet 103b and the elastic strip members 121, 122 can be joined together. For example, the adhesive may be applied to just the sheet 103b, or to both the elastic strip members 121, 122 and the sheet 103b.

REFERENCE SIGNS LIST 1 disposable diaper (absorbent article),
1a front torso area, 1b crotch area, 1c back torso area, 2 surface sheet,
3 back face sheet, 3a inner sheet, 3b outer sheet, 4 absorbent body,
10 around-leg convex portion, 11 end edge portion flaps,
12 side edge portion flaps, 16 torso elastic member,
21 front elastic strip member, 22 back elastic strip member,
30 manufacturing apparatus, 30a manufacturing apparatus,
30b manufacturing apparatus, 30c manufacturing apparatus,
40 slitting apparatus, 40a rotating blade, 40b rotating blade,
50 transporting roll, 60 first guide member,
61 first oscillating arm, 61a oscillating end,
63 first oscillating end side roller,
64 first spindle portion side roller,
65 first spindle portion, 66 outer cylindrical member,
67 bearings, 70 drive mechanism, 72 motor, 72a drive rotational axis,
74 crank mechanism, 75 disk member, 76 link member, 78 coupling pin,
90 reversal roller, 92 support wall,
103b sheet (continuous body of sheet), 120 sheet member,
121 first elastic strip member (continuous body of first elastic strip member),
121a portion, 122 second elastic strip member (continuous body of second elastic strip member),
160 second guide member, 161 second oscillating arm, 161a oscillating end,
161h through hole, 163 second oscillating end side roller,
164 second spindle portion side roller, 165 second spindle portion,
165h through hole, 166 outer cylindrical member, 167 bearings,
170 drive mechanism, 172 motor, 174 crank mechanism,
CL center line, C50 rotational axis, C63 rotational axis,
C64 rotational axis, C65 rotational central axis,
C163 rotational axis, C164 rotational axis, C165 rotational central axis, R121 first supply route, R122 second supply route,
P1 first placing position, P2 second placing position,
P3 position, P4 position, Ps wraparound starting position,
Pe wraparound end position, Pm middle position, PP power point,
R region, Dc circumferential direction

The invention claimed is:

1. An apparatus for manufacturing a composite sheet of an absorbent article by joining a continuous body of an elastic strip member in a predetermined meander pattern to a continuous body of a sheet continuously transported in a transporting direction, the apparatus comprising:
   a first guide member configured to join a continuous body of a first elastic strip member to a continuous body of a sheet by feeding and surface-contacting the continuous body of the first elastic strip member to the continuous body of the sheet, via a first oscillating arm configured to oscillate in a direction intersecting the transporting direction with a first spindle portion as a swivel center; and
   a second guide member configured to join a continuous body of a second elastic strip member to the continuous body of the sheet by feeding and surface-contacting the continuous body of the second elastic strip member to the continuous body of the sheet, via a second oscillating arm configured to oscillate in a direction intersecting the transporting direction with a second spindle portion as a swivel center,
   wherein the first oscillating arm includes a first oscillating end side roller provided to an oscillating end side of the first oscillating arm and a first spindle portion side roller provided to the first spindle portion side,
   wherein the second oscillating arm includes a second oscillating end side roller provided to an oscillating end side of the second oscillating arm and a second spindle portion side roller provided to the second spindle portion side,
   wherein the apparatus is configured such that the continuous body of the first elastic strip member supplied toward the first spindle portion side roller through a first supply route is subsequently, put around an outer circumferential face of the first spindle portion side roller and an outer circumferential face of the first oscillating end side roller, and, after being reversed in a travel direction with the first oscillating end side roller, is placed on the continuous body of the sheet and joined thereon,
   wherein the apparatus is configured such that the continuous body of the second elastic strip member supplied toward the second spindle portion side roller through a second supply route is subsequently put around an outer circumferential face of the second spindle portion side roller and an outer circumferential face of the second oscillating end side roller, and, after being reversed in the travel direction with the second oscillating end side roller, is placed on the continuous body of the sheet and joined thereon,
   wherein the apparatus is configured such that a first placing position where the continuous body of the first elastic strip member is to be placed on the continuous body of the sheet with the first oscillating arm and a second placing position where the continuous body of the second elastic strip member is to be placed on the continuous body of the sheet with the second oscillating arm are different from each other in the transporting direction.

2. The apparatus according to claim 1, further comprising a transporting roll configured to rotate around a predetermined rotational axis,
   wherein the apparatus is configured such that the continuous body of the sheet is wrapped in a predetermined wraparound angle around an outer circumferential face of the transporting roll with a direction along the transporting direction as a circumferential direction, and transported,
   wherein both the first placing position of the first oscillating arm and the second placing position of the second oscillating arm are set within a range of the wraparound angle,
   wherein the second placing position is set to a downstream side than the first placing position in the circumferential direction,
   wherein the second oscillating arm is arranged in a position where the first oscillating arm has rotationally moved to a downstream side in the circumferential direction by only a predetermined rotating angle (excluding 0° and 360°) around an imaginary axis parallel to the rotational axis of the transporting roll.

3. The apparatus according to claim 2, wherein the rotating angle is an arbitrary value in a range of 30° to 150°.

4. The apparatus according to claim 1, further comprising a transporting roll configured to rotate around a predetermined rotational axis,
   wherein the apparatus is configured such that the continuous body of the sheet is wrapped in a predetermined wraparound angle around an outer circumferential face of the transporting roll with a direction along the transporting direction as a circumferential direction, and transported,
   wherein both the first placing position of the first oscillating arm and the second placing position of the second oscillating arm are set within the wraparound angle range,
   wherein a rotational central axis of the first spindle portion of the first oscillating arm and a rotational central axis of the second spindle portion of the second oscillating arm are facing directions intersecting each other in an imaginary plane with the rotational axis direction of the transporting roll as a direction of the normal.

5. The apparatus according to claim 1, further comprising a transporting roll configured to rotate around a predetermined rotational axis,
   wherein the apparatus is configured such that the continuous body of the sheet is wrapped in a predetermined wraparound angle around an outer circumferential face of the transporting roll with a direction along the transporting direction as a circumferential direction, and transported,
   wherein both the first placing position of the first oscillating arm and the second placing position of the second oscillating arm are set in a region to an upstream side than a middle position in the circumferential direction within the wraparound angle.

6. The apparatus according to claim 1,
   wherein the first supply route is along a rotational central axis direction of the first spindle portion of the first oscillating arm,
   wherein the second supply route is along a rotational central axis direction of the second spindle portion of the second oscillating arm.

7. The apparatus according to claim 6,
   wherein the rotational central axis of the first spindle portion of the first oscillating arm is in contact with the outer circumferential face of the first spindle portion side roller of the first oscillating arm, wherein the rotational central axis of the second spindle portion of the second oscillating arm is in contact with the outer circumferential face of the second spindle portion side roller of the second oscillating arm.

8. The apparatus according to claim 1, further comprising a transporting roll configured to rotate around a predetermined rotational axis, wherein the apparatus is configured such that the continuous body of the sheet is wrapped in a predetermined wraparound angle around an outer circumferential face of the transporting roll with a direction along the transporting direction as a circumferential direction, and transported, wherein both the first placing position of the first oscillating arm and the second placing position of the second oscillating arm are set within the wraparound angle range, wherein a first oscillating end side roller and the first spindle portion of the first oscillating arm are arranged to sandwich the rotational axis of the transporting roll together, wherein a second oscillating end side roller and the second spindle portion of the second oscillating arm are arranged to sandwich the rotational axis of the transporting roll together.

\* \* \* \* \*